(12) United States Patent
Targosz

(10) Patent No.: US 8,269,483 B2
(45) Date of Patent: *Sep. 18, 2012

(54) MAGNETIC FLUX TAGGING FOR QUALITY CONSTRUCTION

(76) Inventor: Thomas C. Targosz, New Baltimore, MI (US)

(*) Notice: Subject to any disclaimer, the term of this patent is extended or adjusted under 35 U.S.C. 154(b) by 557 days.

This patent is subject to a terminal disclaimer.

(21) Appl. No.: 12/510,659

(22) Filed: Jul. 28, 2009

(65) Prior Publication Data

US 2009/0287423 A1 Nov. 19, 2009

Related U.S. Application Data

(63) Continuation-in-part of application No. 11/935,605, filed on Nov. 6, 2007, now Pat. No. 7,923,992, which is a continuation of application No. 10/808,750, filed on Mar. 25, 2004, now Pat. No. 7,148,678, and a continuation of application No. 11/608,979, filed on Dec. 11, 2006, now Pat. No. 7,327,136.

(60) Provisional application No. 60/864,422, filed on Nov. 6, 2006, provisional application No. 60/864,479, filed on Nov. 6, 2006, provisional application No. 60/870,984, filed on Dec. 20, 2006, provisional application No. 60/946,447, filed on Jun. 27, 2007, provisional application No. 60/975,550, filed on Sep. 27, 2007, provisional application No. 61/104,857, filed on Oct. 13, 2008, provisional application No. 61/084,072, filed on Jul. 28, 2008, provisional application No. 60/457,772, filed on Mar. 26, 2003, provisional application No. 60/803,140, filed on May 25, 2006.

(51) Int. Cl.
*G01N 27/74* (2006.01)
*G01R 33/12* (2006.01)

(52) U.S. Cl. .................. 324/204; 73/64.42; 73/53.07

(58) Field of Classification Search .................. 324/204; 73/61.42, 53.07
See application file for complete search history.

(56) References Cited

U.S. PATENT DOCUMENTS

| | | | |
|---|---|---|---|
| 4,686,469 A | 8/1987 | Lewis | |
| 4,816,758 A | 3/1989 | Theissen et al. | |
| 5,315,243 A | 5/1994 | Kempster et al. | |
| 5,831,151 A | 11/1998 | Ondrus et al. | |
| 6,560,544 B1 | 5/2003 | Ondrus | |
| 7,327,136 B2 | 2/2008 | Targosz | |

*Primary Examiner* — Reena Aurora
(74) *Attorney, Agent, or Firm* — Fraser Clemens Martin & Miller LLC; William J. Clemens

(57) ABSTRACT

A system and a method for monitoring a building material are disclosed. The system and the method provide a comprehensive monitoring throughout a manufacturing and an application process and provide a real time data feedback relating to the physical characteristics of the building material. The system and method include mixing a predetermined amount of taggant particles with a predetermined volume of at least one component of the building material in order to comprehensively monitor a mix ratio and segregation of the building material during manufacturing and application.

15 Claims, 6 Drawing Sheets

MAGNETIC FLUX TAGGING FOR QUALITY CONSTRUCTION

CROSS-REFERENCE TO RELATED APPLICATION

This application is a continuation-in-part of U.S. patent application Ser. No. 11/935,605, filed on Nov. 6, 2007, which is a continuation of U.S. patent application Ser. No. 10/808,750, filed on Mar. 25, 2004, now U.S. Pat. No. 7,148,678, and U.S. patent application Ser. No. 11/608,979 filed on Dec. 11, 2006, now U.S. Pat. No. 7,327,136 and claims the benefit of U.S. provisional patent application Ser. Nos.: 60/457,772 filed Mar. 26, 2003; 60/803,140 filed May 25, 2006; 60/864,422 filed Nov. 6, 2006; 60/864,479 filed Nov. 6, 2006; 60/870,984 filed Dec. 20, 2006; 60/946,447 filed Jun. 27, 2007; 60/975,550 filed Sep. 27, 2007, 61/084,072 filed Jul. 28, 2008, and 61/104,857 filed Oct. 13, 2008.

FIELD OF THE INVENTION

The present invention relates to magnetic flux tagging. More particularly, the invention is directed to a system and method for real time comprehensive monitoring of road and building materials during all phases of manufacturing and application.

BACKGROUND OF THE INVENTION

Typical asphalt manufactures produce hundreds of tons of asphalt each hour. In certain instances, manufacturers will ship hundreds of tons of "out of specification" material resulting in premature failure of the final roads. An unacceptable alternative to shipping the "out of specification" material is to dump the material at great financial lost to the manufacturer.

A minimal number of tests are performed to ensure the road and building materials are properly mixed. Typically, only a few pounds of asphalt are tested when hundreds of tons of asphalt are manufactured every hour. After a road is installed, a spot test is randomly performed using a nuclear density test or other spot test that requires significant time per test and is unreliable. In particular, a nuclear test is performed by a licensed technician and requires a calibration of the equipment to a sample section of road. However, there is no way to know if the sample road is within specification. Every road or different sections of roads require a new master. Further, the testing materials used in the nuclear test are dangerous. The current non-nuclear spot testing procedures are also calibrated using part of the non-tested road under the assumption that the calibration part is manufactured correctly.

Occasionally the Department of Transportation (DOT) utilizes a sampling technique where a pie-plate type container is positioned on the road wherein the container is filled, compacted, removed, and saved for later examining at the DOT's laboratory. This sampling technique often takes months to determine if the asphalt is within an acceptable mix ratio. As a result of the tested sample, roads having unacceptable mix ratios or segregation must be removed at great expense.

Additionally, a core test involves removing a cylinder shaped specimen directly from the road under test. The specimen must be returned to the laboratory where liquid asphalt is burned off. Subsequently, each of the individual components are separated and weighed. The core test is very time consuming, environment unfriendly, and requires a direct damage to the road.

None of the conventional tests produce real time results. Specifically, the spot test requires several seconds and relies on calibration to a section of road which is not clearly within specification. The core test and pie-plate test require days or weeks to evaluate. When hundreds of tons of asphalt are manufactured each hour any of these tests are too little and too late. Further, there is currently no real time testing during shipment or transport when heavy stones are known to separate due to the vibration nature of transporting.

There is no present technology which comprehensively inspects the manufacturing of a road. The primary reason for failed roads is the segregation. There are no absolute technologies which monitor mixing liquid asphalt with polymer, aggregate with binder, shipping of binder, shipping of asphalt concrete, compaction of road during installation, monitoring of cracks in roads, or laboratory specimen monitoring. No conventional technology provides the correlation of every manufacturing process. There is no current technology which monitors in real-time all previously mentioned manufacturing processes. Currently, segregation is not detected until after a road is compacted and manufactured.

It would be desirable to have a system and a method for monitoring a building material, wherein the system and the method are comprehensive throughout the manufacturing and application processes and provide a real time data feedback relating to the physical characteristics of the building material.

SUMMARY OF THE INVENTION

Concordant and consistent with the present invention, a system and a method for monitoring a building material, wherein the system and the method are comprehensive throughout the manufacturing and application processes and provide a real time data feedback relating to the physical characteristics of the building material, has surprisingly been discovered.

One object of the present invention is to provide a comprehensive inspection of all manufacturing and application processes relating to road construction.

Another object of the present invention is to provide real time monitoring of each stage of a manufacturing and application process relating to road construction.

Another object of the present invention is to provide absolute monitoring of a mix ratio while: mixing a liquid asphalt with a polymer, mixing an aggregate with a binder; shipping the binder; shipping an asphalt; and compacting a road during installation.

Further, an object of the present invention is to provide a real time monitoring of: cracks in roads; segregation of the components of the road material; and inconsistencies in the acceptable density of the components of the road material as a result of compaction.

In one embodiment, a batch tester comprises: a hopper for receiving a mixture including a volume of taggant particles; a sensor for generating a sense signal representing an amount of taggant particles in a volume of the mixture within a field-of-view of the sensor; and a processor for receiving the sense signal and calculating a ratio of taggant particles relative to the volume of the mixture flowing within a field-of-view of the sensor.

The present invention also provides methods for monitoring a building material.

One method comprises the steps of:
a. mixing a predetermined amount of taggant particles with a predetermined first volume of a first component of a building material to prepare a first mixture in a first mixing device;

b. providing a first sensor for generating a first sense signal representing an amount of taggant particles per unit volume of the first mixture flowing into a second mixing device;
c. mixing a predetermined second volume of a second component of the building material with the first mixture to prepare a second mixture in the second mixing device;
d. providing a second sensor generating a second sense signal representing an amount of taggant particles per unit volume of the second mixture flowing from the second mixing device;
e. providing a processor for calculating a ratio of the volumes of the first and second components in the second mixture in response to the first and second sense signals;
f. dispensing the second mixture onto a surface; and
g. scanning the second mixture disposed on the surface.

Another method comprises the steps of:
a. mixing a predetermined amount of taggant particles with a predetermined first volume of a first component of a building material to prepare a first mixture in a first mixing device;
b. providing a first sensor for generating a first sense signal representing an amount of taggant particles per unit volume of the first mixture;
c. transporting the first mixture to a second mixing device;
d. mixing a predetermined second volume of a second component of the building material with the first mixture to prepare a second mixture in the second mixing device;
e. providing a second sensor generating a second sense signal representing an amount of taggant particles per unit volume of the second mixture flowing from the second mixing device;
f. providing a processor for calculating a ratio of the volumes of the first and second components in the second mixture in response to the first and second sense signals;
g. transporting the second mixture to a dispensing site;
h. dispensing the second mixture onto a surface located at the dispensing site;
i. compacting the second mixture on the surface to form a finished road; and
j. scanning the finished road.

BRIEF DESCRIPTION OF THE DRAWINGS

The above, as well as other advantages of the present invention, will become readily apparent to those skilled in the art from the following detailed description of the preferred embodiment when considered in the light of the accompanying drawings in which.

DETAILED DESCRIPTION OF EXEMPLARY EMBODIMENTS OF THE INVENTION

The following detailed description and appended drawings describe and illustrate various embodiments of the invention. The description and drawings serve to enable one skilled in the art to make and use the invention, and are not intended to limit the scope of the invention in any manner. In respect of the methods disclosed, the steps presented are exemplary in nature, and thus, the order of the steps is not necessary or critical.

Figure 1:
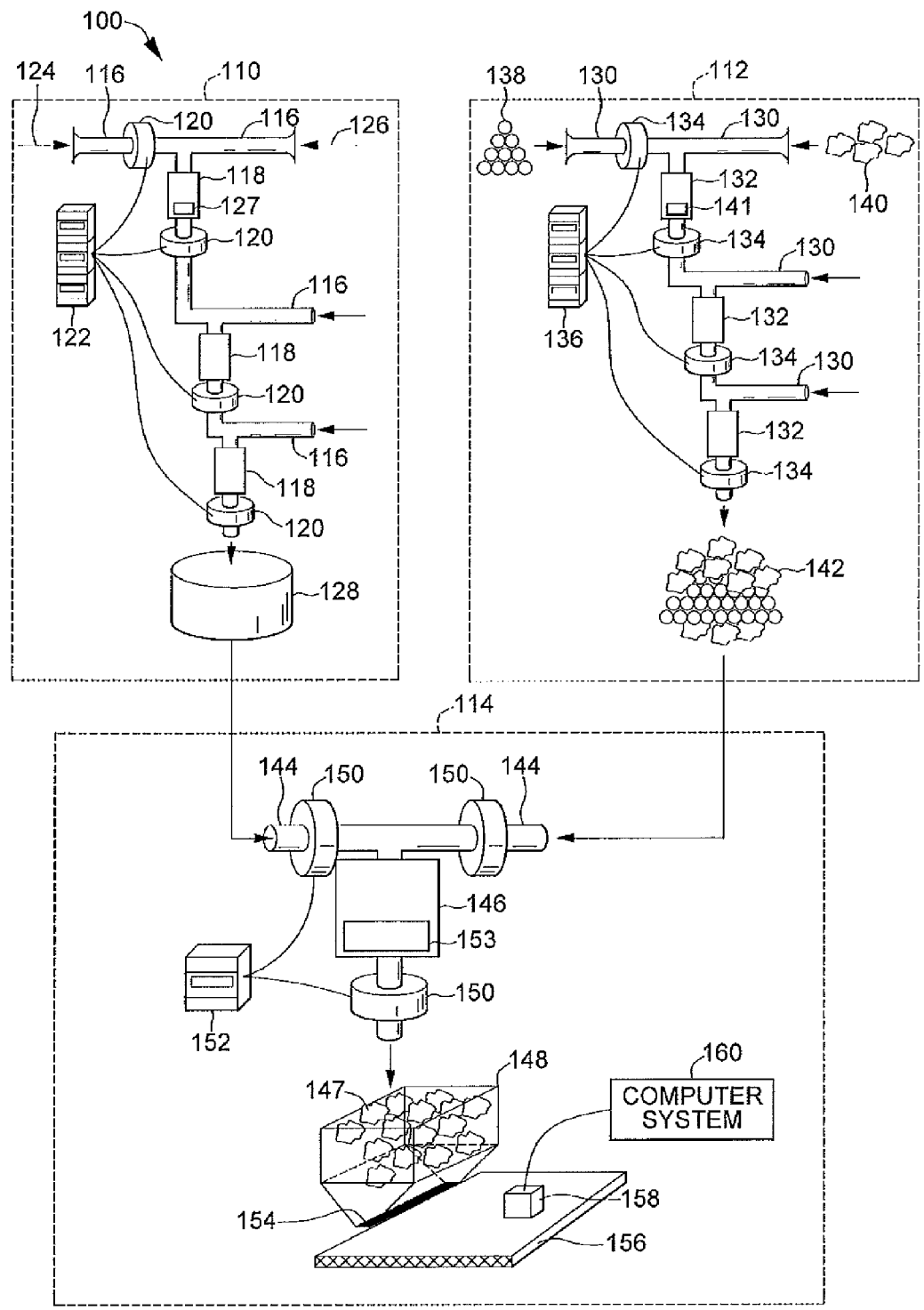
FIG. 1 is a schematic diagram of a tagging system according to an embodiment of the present invention.

FIG. 1 illustrates a system 100 for tagging and monitoring materials used in roadway construction. It is understood that the system 100 may be similar to the systems described in U.S. Pat. Nos. 7,148,678 and 7,327,136, the entire disclosures of which are hereby incorporated herein by reference. It is further understood that the system 100 may be applied to any roadway and building materials such as asphalt, concrete, cement, plastics, and other aggregate mixtures. As shown, the system 100 includes a first mixing subsection 110, a second mixing subsection 112, and a third mixing subsection 114.

The first mixing subsection 110 includes a plurality of mixing inlets 116, a plurality of component mixers 118, a plurality of sensors 120, and a processor 122. Each of the mixing inlets 116 receives a pre-determined material component and directs the component to the mixers 118 to be combined. In certain embodiments, one of the mixing inlets 116 receives a taggant component 124 and another one of the mixing inlets 116 receives a non-taggant component 126. As a non-limiting example, the taggant component 124 includes a constant known amount of ferrous taggant particles per unit volume. As a further example, the taggant component 124 may include at least one of a liquid asphalt and a polymer. However, other road materials and binding agents may be used.

The mixing inlets 116 converge and flow into one of the mixers 118. As shown, each of the mixers 118 is adapted to receive components from two sources. However, the mixers 118 may receive any number of source components as desired. It is understood that any number of mixers 118 and mixing inlets 116 may be used. It is further understood that the mixers 118 may include a feed screw and motor for mixing the components 124, 126 and ensuring a substantially constant pre-pressure to the materials. In certain embodiments, the mixers 118 include a feedback mix sensor 127 for scanning the components 124, 126 in the mixers 118 to determine when the components 124, 126 are optimally mixed.

The sensors 120 are adapted to monitor the components prior to mixing and after mixing. In the embodiment shown, each of the sensors 120 is an encircling sensor mounted in such a manner that the taggant component 124, carrying a constant known amount of ferrous taggant particles per unit volume, flows through a center of the sensors 120. It is understood that the taggant is not restricted to ferrous, ferrite, or a high permeability material. Due to eddy current effects, any conductive material may be used such as copper and aluminum, which may not have high permeability. Thus, the sensors 120 determine that a desired amount of taggant particles is flowing therethrough. When the two components 124, 126 are mixed in the mixers 118, a first resultant mixture 128 is produced and flows through the center of at least one of the sensors 120.

The processor 122 is in communication with each of the sensors 120. As a non-limiting example, the processor 122 may be any processing device such as a personal computer (PC), a programmable logic controller (PLC), and may include a diagnostic display. The processor 122 provides information as to the operation of the system 100 and can use the information generated by the sensors 120 in a feedback control system to automatically adjust the flow of the components 124, 126 through the mixing inlets 116. In particular, the passage of the ferrous taggant particles of the taggant component 124 is detected by the sensors 120 which each send a sensor signal to the processor 122. In certain embodiments, the sensors 120 detect a percentage of the taggant component 124 based on a total amount of material within the sensor's "footprint" or field of scan. It is understood that the percentage is a function of density and mix ratio. It is further understood that this percentage may be used to calculate a future percentage based upon known amounts of total material, thereby establishing tolerance of acceptable mixes. After demodulation of the sensor signal, a linear output signal proportional to the amount of ferrous taggant particles is generated by the processor 122. It is understood that a non-linear output signal may be generated to represent the amount of ferrous taggant particles in a volume of the components 124, 126. A delay representing the time required for the portion of the taggant component 124, previously measured with one sensor 120, to move within another one of the sensors 120 is required. This delay allows the taggant component 124 to mix with the non-taggant component 126 and move within another one of the sensor 120. This will assure testing of the components 124, 126 before and after mixing.

In certain embodiments, the change in electrical response has been determined to be linear with respect to amount of taggant, which simplifies the resultant ratio equations. Additionally, using a deviation from a desired ratio will further eliminate errors due to different mixtures of the components 124, 126. If for instance the mixture has been reduced by ten percent, the comparative readings of one of the sensors 120 to another one of the sensors 120 will be reduced proportionally. Thus, the mixture will still have the correct ratio. Additionally, the absolute reading of the sensor 120 disposed at an output of the mixer 118 is monitored to assure the mixture is held within a certain percent. As a non-limiting example, the sensing and analysis of the resultant measurements may be similar to the methods described by U.S. Pat. Nos. 7,148,678 and 7,327,136.

The second mixing subsection 112 includes a plurality of mixing inlets 130, a plurality of mixers 132, a plurality of sensors 134, and a processor 136. Each of the mixing inlets 130 receives a pre-determined component and directs the component to the mixers 132 to be combined. In certain embodiments, one of the mixing inlets 130 receives a taggant component 138 and another one of the mixing inlets 130 receives a non-taggant component 140. As a non-limiting example, the taggant component 138 includes a constant known amount of ferrous taggant particles per unit volume. It is understood that the taggant is not restricted to ferrous, ferrite, or a high permeability material. Due to eddy current effects, any conductive material may be used such as copper and aluminum, which may not have high permeability. It is further understood that a ratio of ferrous taggant particle per unit volume may be different from the first taggant component 124 in order to differentiate the sensing of the first taggant component 124 from the second taggant component 138. In certain embodiments, separate masters may be used to calibrate the sensors 120, 134, 150 based upon any pre-determined ratio of taggant particle per unit volume. As a further example, the taggant component 138 may include at least one of a sand and an aggregate material. However, other road materials and building agents may be used.

The mixing inlets 130 converge and flow into one of the mixers 132. As shown, each of the mixers 132 is adapted to receive components from two sources. However, the mixers 132 may receive any number of source components as desired. It is understood that any number of mixers 132 and mixing inlets 130 may be used. It is further understood that the mixers 132 may include a feed screw and motor for mixing the components 138, 140 and ensuring a substantially constant pre-pressure to the materials. In certain embodiments, the mixers 132 include a feedback mix sensor 141 for scanning the components 138, 140 in the mixers 132 to determine when the components 138, 140 are optimally mixed.

The sensors 134 are adapted to monitor the components prior to mixing and after mixing. In particular, each of the sensors 134 is an encircling sensor mounted in such a manner that the taggant component 138, carrying a constant known amount of ferrous taggant particles per unit volume, flows through the center of the sensors 134. Thus, the sensors 134 determine that a desired amount of taggant particles is flowing. The non-taggant component 140 has no ferrous particles. When the two components 138, 140 are mixed in the mixers 132, a second resultant mixture 142 is produced and flows through the center of at least one of the sensors 134.

The processor 136 is in communication with each of the sensors 134. As a non-limiting example, the processor 136 may be any processing device such as a personal computer (PC), a programmable logic controller (PLC), and may include a diagnostic display. The processor 136 provides information as to the operation of the system 100 and can use the information generated by the sensors 136 in a feedback control system to automatically adjust the flow of the components 138, 140 through the mixing inlets 130. In particular, the passage of the ferrous taggant particles of the taggant component 138 is detected by the sensors 134 which each send a sensor signal to the processor 136. In certain embodiments, the sensors 134 detect a percentage of the taggant component 138 based on a total amount of material within the sensor's "footprint" or field of scan. It is understood that the percentage is a function of density and mix ratio. It is further understood that this percentage may be used to calculate a future percentage based upon known amounts of total material, thereby establishing tolerance of acceptable mixes. After demodulation of the sensor signal, a linear output signal proportional to the amount of ferrous taggant particles is generated by the processor 136. It is understood that a non-linear output signal may be generated to represent the amount of ferrous taggant particles in a volume of the components 138, 140. The sensing and measurement of the sensors 134 and associated processor 136 function in the same manner as the sensors 120 and processor 122 of the first mixing subsection 110.

The third mixing subsection 114 is adapted to combine and mix the resultant mixtures 128, 142 of the first subsection 110 and the second subsection 112. The third subsection 114 includes a plurality of mixing inlets 144, a batch mixer 146 to produce a final mixture 147, a hopper 148, a plurality of sensors 150, and a processor 152.

Each of the mixing inlets 144 receives a pre-determined component and directs the component to the batch mixer 146 to be combined. It is understood that the batch mixer 146 may include a feed screw and motor for combining the resultant mixtures 128, 142 and ensuring a substantially constant pre-pressure to the materials. In certain embodiments, one of the mixing inlets 144 receives the first resultant mixture 128 from the first mixing subsection 110 and another one of the mixing inlets 144 receives the second resultant mixture 142 from the second mixing subsection 112.

The sensors 150 are adapted to monitor the resultant mixtures 128, 142 prior to mixing and after mixing. In particular, each of the sensors 150 is an encircling sensor mounted in such a manner that the resultant mixtures 128, 142, each carrying a constant known amount of ferrous taggant particles per unit volume, flow through the center of the sensors 150. Thus, the sensors 150 determine that a desired amount of taggant particles is flowing in each of the resultant mixtures 128, 142. When the two resultant mixtures 128, 142 are mixed in the batch mixer 146, the final mixture 147 results and flows through the center of at least one of the sensors 150. It is understood that the at least one of the sensors 150 may be calibrated based upon a master associated with any one of the resultant mixtures 128, 142. Other calibration may be used, as desired. In certain embodiments, the batch mixer 146 include a feedback mix sensor 153 for scanning the resultant mixtures 128, 142 to determine when the components of the mixtures are optimally mixed.

The processor 152 is in communication with each of the sensors 150. As a non-limiting example, the processor 152 may be any processing device such as a personal computer (PC), a programmable logic controller (PLC), and may include a diagnostic display. The processor 152 provides information as to the operation of the system 100 and can use the information generated by the sensors 150 in a feedback control system to automatically adjust the flow of the resultant mixtures 128, 142 through the mixing inlets 144. In particular, the passage of the ferrous taggant particles in each of the mixtures 128, 142, 147 is detected by the sensors 150 which each send a sensor signal to the processor 152. In certain embodiments, the sensors 150 detect a percentage of the taggant components 124, 138 based on a total amount of material within the sensor's "footprint" or field of scan. It is understood that the percentage is a function of density and mix ratio. It is further understood that this percentage may be used to calculate a future percentage based upon known amounts of total material, thereby establishing tolerance of acceptable mixes. After demodulation of the sensor signal, a linear output signal proportional to the amount of ferrous taggant particles is generated by the processor 152. It is understood that a non-linear output signal may be generated to represent a ratio of ferrous taggant particles per unit volume.

In the embodiment shown, the final mixture 147 is stored in the hopper 148 for subsequent transport or dispensing. Similar to the sensors 150 described above, a hopper sensor 154 is disposed in the hopper 154 to detect the taggant particles in the final mixture 147 for determining a mix ratio and segregation of the components of the final mixture 147. It is understood that the hopper sensor 154 may be in communication with the processor 152 for transfer and analysis of collected data. It is further understood that the hopper sensor 154 is transported with the hopper 148 to a construction site and any processing device may be in communication with the hopper sensor 154 to retrieve the collected data. As a non-limiting example the hopper sensor 154 may be adapted to sense a density of the final mixture 147 during a compaction thereof. In certain embodiments, a ratio of ferrous taggant particle per unit volume in the first resultant mixture 128 may be different from the second resultant mixture 142 in order to differentiate the sensing of the first taggant component 124 from the second taggant component 138.

Once the hopper 148 is at a pre-determined site, the final mixture 147 is dispensed onto a surface. In certain embodiments, the final mixture 147 is compacted to form a finished road 156. As shown, a road sensor 158 may be used to scan the finished after dispensing or compaction. As a non-limiting example, the road sensor 158 may be a winding sensor disposed on a scan vehicle, which is driven over a top surface of the finished road 156 to be scanned. As a further example, the road sensor 158 is submerged within the finished road 156 or under the finished road 156. As such, a computer system 160 or processor is interconnected to the road sensor 158 to retrieve real time data therefrom. In certain embodiments, the submerged road sensor 158 is adapted to make measurements in response to a load on the top surface of the finished road 156. It is understood that a conventional core specimen of the finished road 156 may be scanned and tested on-site using an encircling sensor similar to the sensors 120, 134, 150, thereby providing real time data on-site. It is further understood that the encircling sensor may have any diameter in order to receive any core specimen size.

Figure 2:
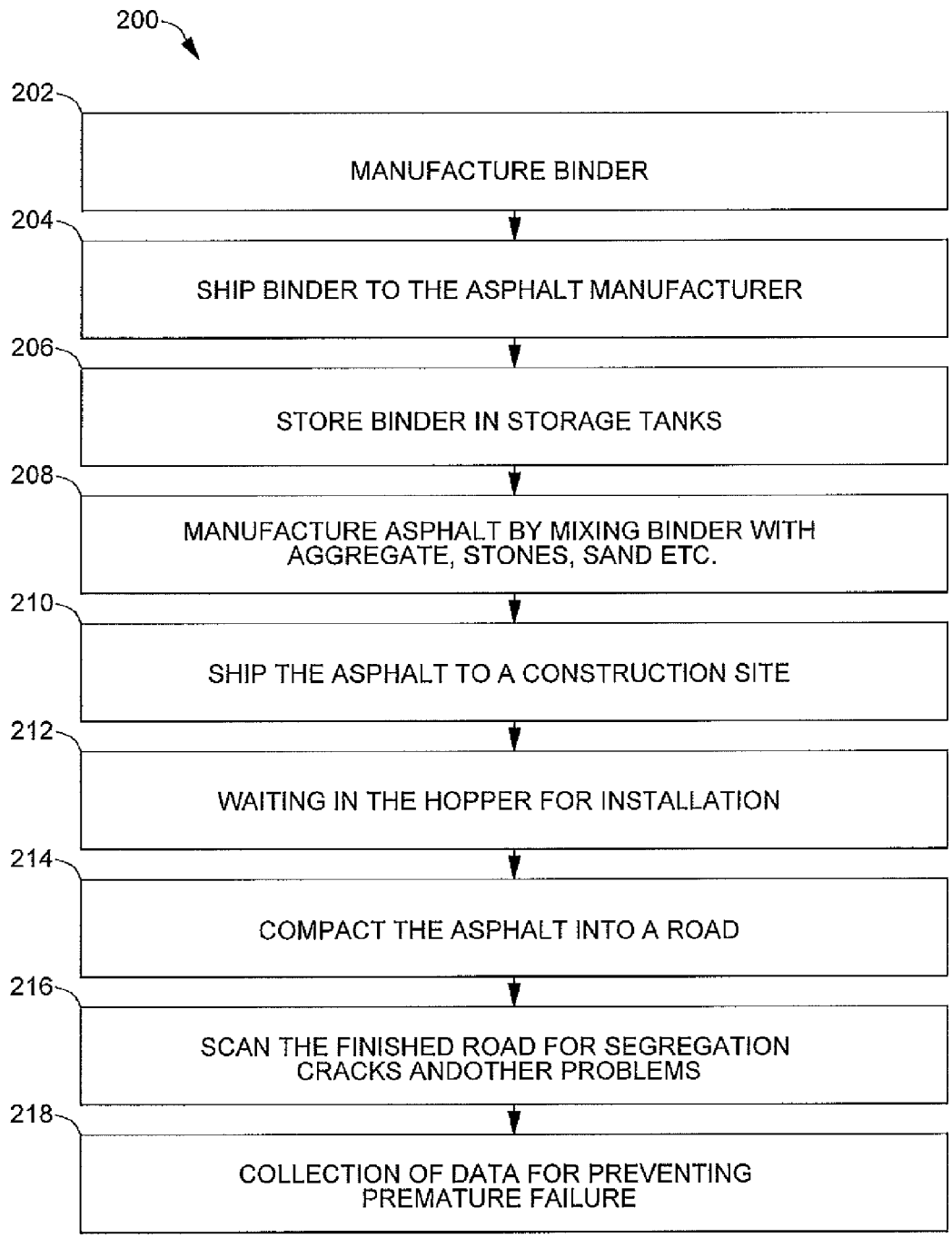
FIG. 2 is a schematic block diagram of a method for monitoring a building material according to an embodiment of the present invention.

FIG. 2 illustrates a method 200 for monitoring a building material according to an embodiment of the present invention. The method 200 is initiated by manufacturing a binder, as illustrated in step 202. As a non-limiting example, the binder is a liquid asphalt component that will eventually be mixed with aggregate. In certain embodiments, the binder acts as a binding agent that holds an asphalt road together. Various additives can be mixed with liquid asphalt such as polymer to control the binding characteristics. The addition of a tagged material to a binder ensures the binder is properly mixed with the polymers or other additives. The addition of a tagged material will create the taggant component 124 described above, which provides a baseline for the remaining testing during and after manufacturing. It is understood that an average value is the mix ratio and the standard deviation provides information on how well it is mixed. First the binder is manufactured using various grades of liquid asphalt. Liquid asphalt is often mixed with polymer. The polymer must initially be mixed with the liquid asphalt. Today's technology relies on adjusting flow rates to ensure the mixing. Flow rate indicators are subject to wearing out. The operator compensates for the slowly reacting flow meter with increased volume which results in off ratio materials. Operator errors and leaks are other sources of flow rate error. The method 200 provides an absolute measurement of mix ratio. An encircling sensor monitors the mixture as it is piped through an inner diameter of the sensor. The sensors accurately measure the mix ratio during binder manufacturing as well as during shipment. Additional sensors monitor the binder as it is dispensed into the batch mixer and as it mixes with the aggregate for asphalt concrete.

The method 200 continues to step 204, wherein the binder is transported to an asphalt manufacturer. Before and after transport, the binder is held in storage tanks, as shown in step 206. Sensors mounted within the transport vehicle and inside storage tanks at the asphalt manufacturers provide real time monitoring of the binder and the taggant ratio to ensure the binder remains mixed and the segregation does not occur. For example, an operator may be notified if segregation of polymer and binder is detected by the sensors. In certain embodiments, submergible sensors are disposed inside the transport means and in the holding tanks before mixing with aggregate to monitor the binder and detect mix ratio and segregation. Additionally an encircling sensor can monitor the binder before it is mixed with the aggregate.

The method 200 continues to step 208, wherein asphalt is manufactured by mixing the binder with at least one of aggregate, stones, and sand. The binder, aggregate, sand, and stones are inspected at the manufacturing plant to ensure they are properly mixed at the onset, before leaving the manufacturing plant, thereby ensuring a quality is traceable back to the manufacturer. It is understood that hundreds of tons of asphalt are manufactured every hour by mixing the binder with the aggregate. Asphalt manufacturing relies on batch or drum mixing equipment. If hundreds of tons of asphalt are manufactured per hour eventually a failure will occur. With present technology a failure during production will go unnoticed and result in large amounts of segregated asphalt, since the only testing occurs after the road is installed. Operator errors in selecting the various stones also go unnoticed. The method 200 monitors the mix ratio before mixing, while mixing, and after the mixture is finalized. Any problems will be detected and reported to the operator. It is understood that a road is designed with precision amounts of various sizes stones, sand aggregate. An incorrect size of stone will change the mixtures ratio and be detected with the method 200.

Throughout the method 200, various sensors detect changes which vary linearly corresponding to the changes in the tagged material. For example compacting the material by 10% will directly affect the displayed reading by reducing the volume by 10% and increasing the density according to the change in volume. Another advantage of adding tagged material is in simplifying the calibration by providing masters independent of the material under test (for example the asphalt). By adding the corresponding amount of tagged material to a non-asphalt mixture that is easily reproducible enables us to accurately manufacture and reproduce identical masters. This produces consistency from road to road and state to state when manufacturing an asphalt road. An operator can return to the road years later and monitor the changes which have occurred. Contrary, the various other technologies (ex. spot test, nuclear test, etc.) require mastering on the road under test which is subject to operator errors. The operator must produce a section of road that is manufactured perfectly. It is never known if the road is within specification to begin with and often results in producing roads which are out of specification or incorrect feedback to the asphalt manufacturers which may result in a non-accurate change in the recipe. With current testing methods, there is no accurate way of returning to the road to monitor changes which may occur over time.

The method 200 continues to step 210, wherein the asphalt is transported to a dispensing site or construction site. Sensors are disposed in the transport vehicle to monitor the asphalt during shipment and ensure that the asphalt arrives at the construction site without segregation. This is necessary for optimally manufactured roads. Sensors positioned inside the transport vehicle continuously monitor for segregation. As segregation occurs the stones and sand separate from the tagged liquid asphalt. This is detected by various sensors mounted on the side of the vehicle or submerged within the asphalt itself. Segregation often occurs when delivery is delayed.

The method 200 continues to step 212, wherein the asphalt is awaiting installation inside of a hopper, thereby allowing potential segregation of the combined materials. A plurality of submerged sensors and sensors mounted on a wall of the hopper detect the occurrence of segregation and warn the operator that segregation is occurring.

The method 200 continues to step 214, wherein the asphalt is dispensed and compacted into a finished roadway. As the asphalt is dispensed onto the road a compactor will compact the asphalt until it is at the required density. A plurality of sensors is mounted on the compactor to monitor below the surface to ensure the asphalt is at the proper density and notifying the operator if compaction is outside of their specification. Additionally, the data received from the sensors may be used to notify the operator when the road is optimally compacted.

The method 200 continues to step 216, wherein the finished roadway is scanned for segregation cracks and other inconsistency in the finished road. A finished road can be inspected for segregation and cracks by positioning specially designed sensors on a moving vehicle and scanning the finished road. This enables accurate gathering of data for preventative maintenance and historical records. It eliminates crude methods of removing a sample of the road and later testing at a laboratory. Potholes cracks are monitored and repaired before creating hazards.

The method 200 continues to step 218, wherein data is collected for preventing premature failure. By periodically scanning the roads for changes in cracks and segregation the historical data can be used to ensure roads are properly maintained. Global positioning provides accurate location of problems. Additionally, permanently mounted sensors for monitoring road conditions can be installed to monitor changes in the road or to monitor the effects of transient loads.

In certain embodiments, the collected data along with a study of laboratory specimens are used to manufacture future roads. Specifically, a lab technician hand measures and mixes the components and then makes the specimen by taking the final hand-made mixture and compacting. The specimen is scanned in order to confirm a proper mix. It is understood that a compaction and tensile characteristics may also be scanned in real time. As such, the road designer can study the laboratory specimens. As a non-limiting example, a specimen is a 155 mm puck shaped test block (other shapes and sizes are also used) made of materials used to manufacturer the road. A plurality of laboratory sensors can monitor the behavior of this specimen under load conditions in a laboratory and directly compare to the actual roads characteristic. In essence this closes the design-research-construction loop. It enables the improvements made in a laboratory that are practical road improvements. It answers questions why a section of road is underperforming or prematurely failing without destructive testing even before it prematurely fails.

It is understood that other high permeability components may be added to the building materials. For example, roads are occasionally manufactured with a percentage of the mixture taken from old roads. If this road was previously tagged the final asphalt will exhibit an increase in mix ratio when displayed using Magnetic Flux Tagging instruments. This is a mathematically predictable percent reading based on the amount of used road added. Additionally the standard deviation will ensure the mixture is properly mixed. The new percentage will continue to reflect all the compaction, crack characteristics previously mentioned. Note: Another high permeability material occasionally added to roads is removed from blast furnaces and may contain high permeability ferrous.

As indicated in steps 214-218, the tagged components of the building material may be monitored during application to a surface, compaction, and after the roadway construction is complete. FIGS. 3-8 illustrate examples of roadway monitoring according to the present invention.

Figure 3:
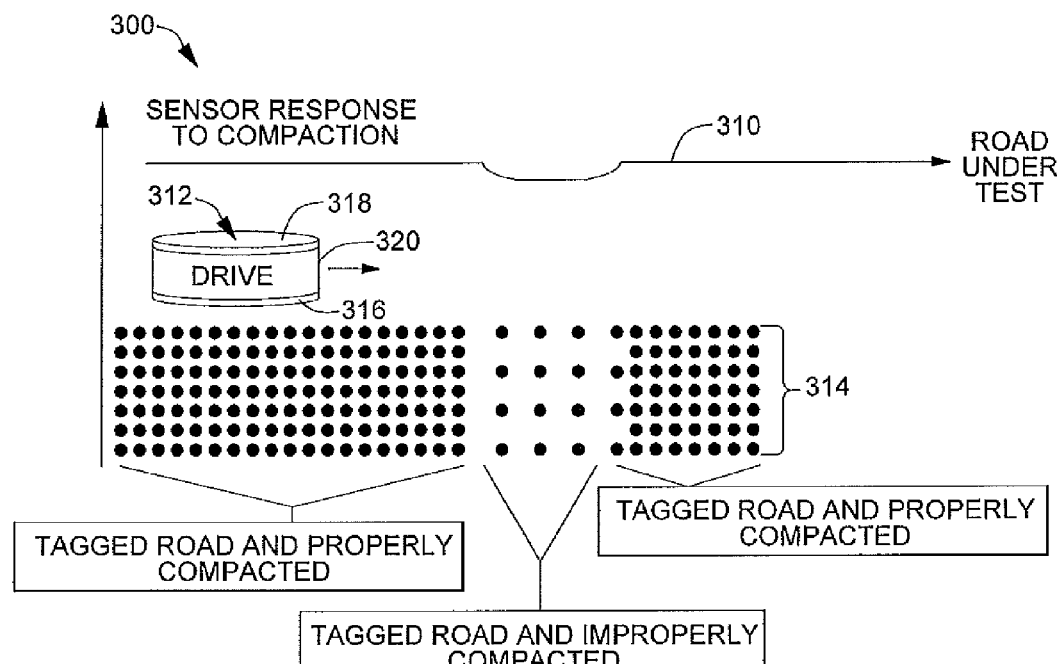
FIG. 3 is a graphical representation of an output of a sensor according to an embodiment of the present invention, illustrating the output in response to compaction of a building material.

FIG. 3 illustrates a graphical representation 300 of a signal output 310 of a dual sense winding compaction and segregation sensor 312 for scanning a tagged road 314. As shown, the compaction and segregation sensor 312 includes a pair of sense windings 316, 318 mounted on opposite sides of a drive winding 320 along an axis perpendicular to the road 314. As such, the drive winding 320 is used to generate and alternating current (AC) magnetic field. The sense windings 316, 318 are wired differentially and the electronics are designed to monitor the difference between a first sensing winding 316 and a second sense winding 318. The sensor 312 is calibrated in air by adding or removing windings or turns from one of the sense windings 316, 318 until no output signal is present after it is amplified. Thereafter, when positioning the sensor 312 on the tagged road surface 314 the signal output 310 is related to the density of the tagged material which has been mixed with the various road components. If segregation occurs the displayed reading will be different from the non-segregated road. As the tagged road 314 is compacted the compaction will increase the density of the tagged material. This is directly proportional to the compaction. The tagged material is much higher in permeability then air and water, enhancing its ability to accurately monitor roads in any environment. In certain embodiments, the sensor 312 is attached to moving vehicles while scanning the tagged road 314. Additionally, an array of the sensors 312 may be sued to scan a full width of a road.

Figure 4:
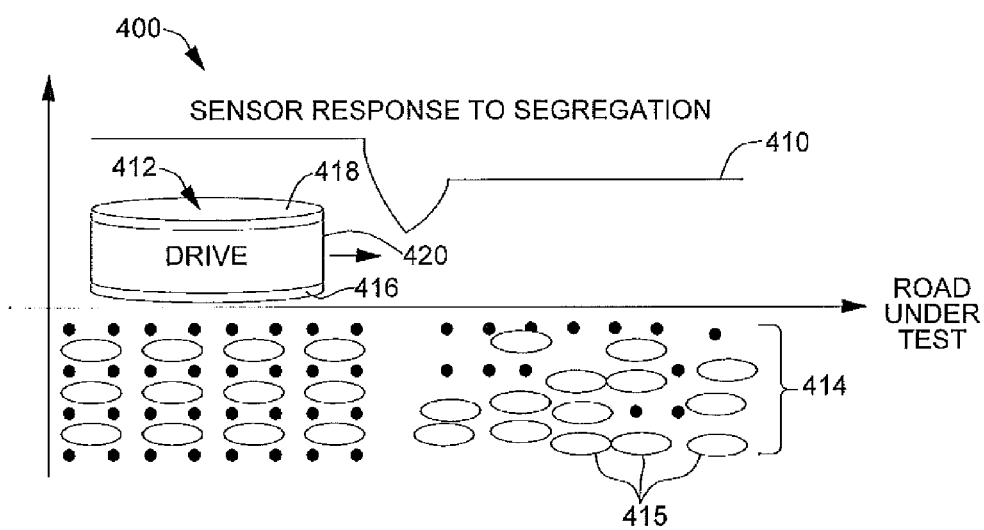
FIG. 4 is a graphical representation of an output of a sensor according to an embodiment of the present invention, showing the output in response to a segregation of a building material.

FIG. 4 illustrates a graphical representation 400 of a signal output 410 of a dual sense winding compaction and segregation sensor 412. As shown, the compaction and segregation sensor 412 is similar to the dual sense winding compaction and segregation sensor 312 of FIG. 3. When positioning the sensor on the tagged road surface 412 the return output signal is related to the density of the tagged material which has been mixed with the various road components. If segregation occurs the signal output 410 will be different from the non segregated road. As a non-limiting example, the winding sensors 312, 412 may consist only of one drive winding, wherein an impedance of the drive winding will vary with the amount of tagged material in the road. As a further example, the winding sensors 312, 412 may include a drive winding with only one sense winding. It is understood that errors caused by lift off can be compensated for by adding distance sensors such as ultrasonic or laser sensors. It is further understood that temperature changes are compensated for by monitoring the temperature of the road and the winding sensors 312, 412.

Figure 5:
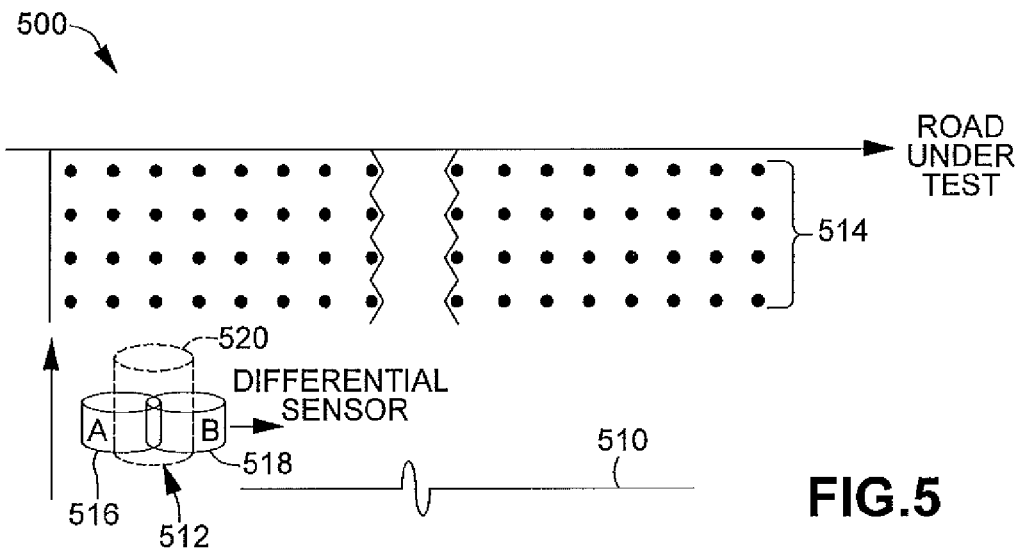
FIG. 5 is a graphical representation of an output of a sensor according to an embodiment of the present invention, illustrating the output in response to a crack in a building material.
Figure 6:
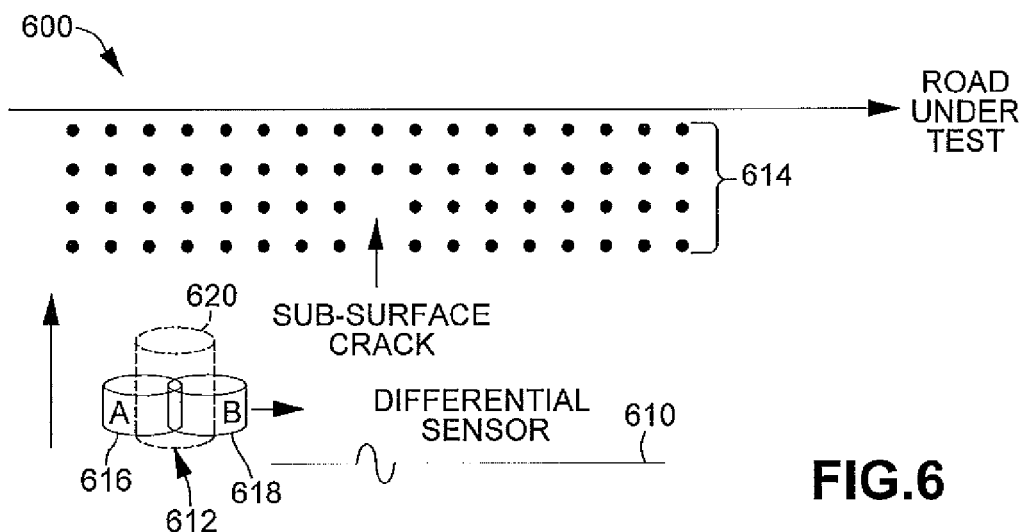
FIG. 6 is a graphical representation of an output of a sensor according to an embodiment of the present invention, showing the output in response to a sub-surface crack in a building material.
Figure 7:
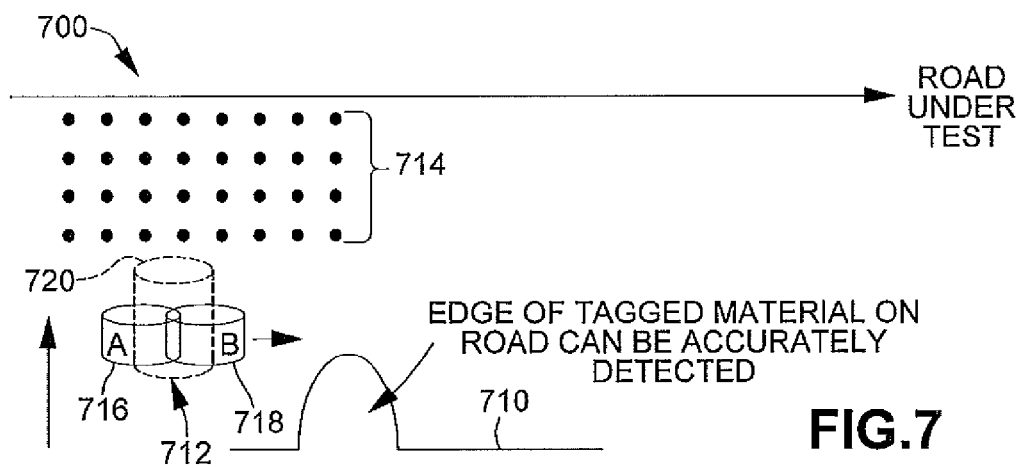
FIG. 7 is a graphical representation of an output of a sensor according to an embodiment of the present invention, illustrating the output in response to an edge of a building material.

FIGS. 5-7 each illustrate a graphical representation 500, 600, 700 of a signal output 510, 610, 710 of a crack detection sensor 512, 612, 712 for monitoring a tagged road 514, 614, 714. The crack detection sensors 512, 612, 712 each include a first sense winding 516, 616, 716, a second sense winding 518, 618, 718, and a drive 520, 620, 720. In certain embodiments, the first sense winding 516, 616, 716 and the second sense winding 518, 618, 718 are position along a horizontal axis. The sense windings 516, 616, 716, 518, 618, 718 are wired differentially. The output is zeroed by positioning the two sense windings 516, 616, 716, 518, 618, 718 in air and adjusting the windings or turns until no signal is present at the output of the amplifier. The signal is canceled whenever the two sense windings 516, 616, 716, 518, 618, 718 are positioned over similar tagged road surfaces. The sensor 512, 612, 712 approaches a crack and is first detected by the second sense winding 518, 618, 718. Then as the sensor 512, 612, 712 moves over the crack, the first sense winding 516, 616, 716 responds at a different time. In particular, an induced voltage is produced proportional to the number of windings and strength of the field. For example, the induced voltage may be modeled by the following equations: v=N df/dt, (wherein N=number of turns and f=flux). A crack is thereby easily recognizable by the pattern exhibited in FIGS. 5-7. Where the crack is wider than a sensor a pulse similar to the signal output 710 will result, thereby causing the signal output to go positive-negative or negative-positive. A width, height, and shape can be used by the computer/operator to characterize the crack, and decide if immediate repair is necessary. Historical data will be collected and analyzed. Changes will be monitored. Errors caused by lift off can be compensated for by adding distance sensors such ultrasonic or laser. Temperature compensation techniques will also adjust to the varying temperature of roads. In certain embodiments, the drive 520, 620, 720 is influenced by a speed of the crack detection sensor 512, 612, 712 relative to the tagged road 514, 614, 714. As such, a speed of the crack detection sensor 512, 612, 712 (or transport vehicle) can be monitored and adjusted for in software. It is understood the crack detection sensor 512, 612, 712 will vary according to the volume of the tagged material displaced by the crack. However, the variations among crack sensors is predictable with software based the size of the sensors footprint, depth of the flux, and speed of the vehicle. It is further understood that multiple sensors can be mounted on a moving vehicle for comprehensive inspection of the road under test.

It should be noted that mounting two crack sensor windings along a linear axis can result in not detecting a crack that is also aligned with the same linear axis. Accordingly, the addition of a third crack sensor ensures at least one set of co-sensor readings will always see a crack. Additionally the absolute reading of each crack sensor contains information regarding the road under test.

Figure 8:
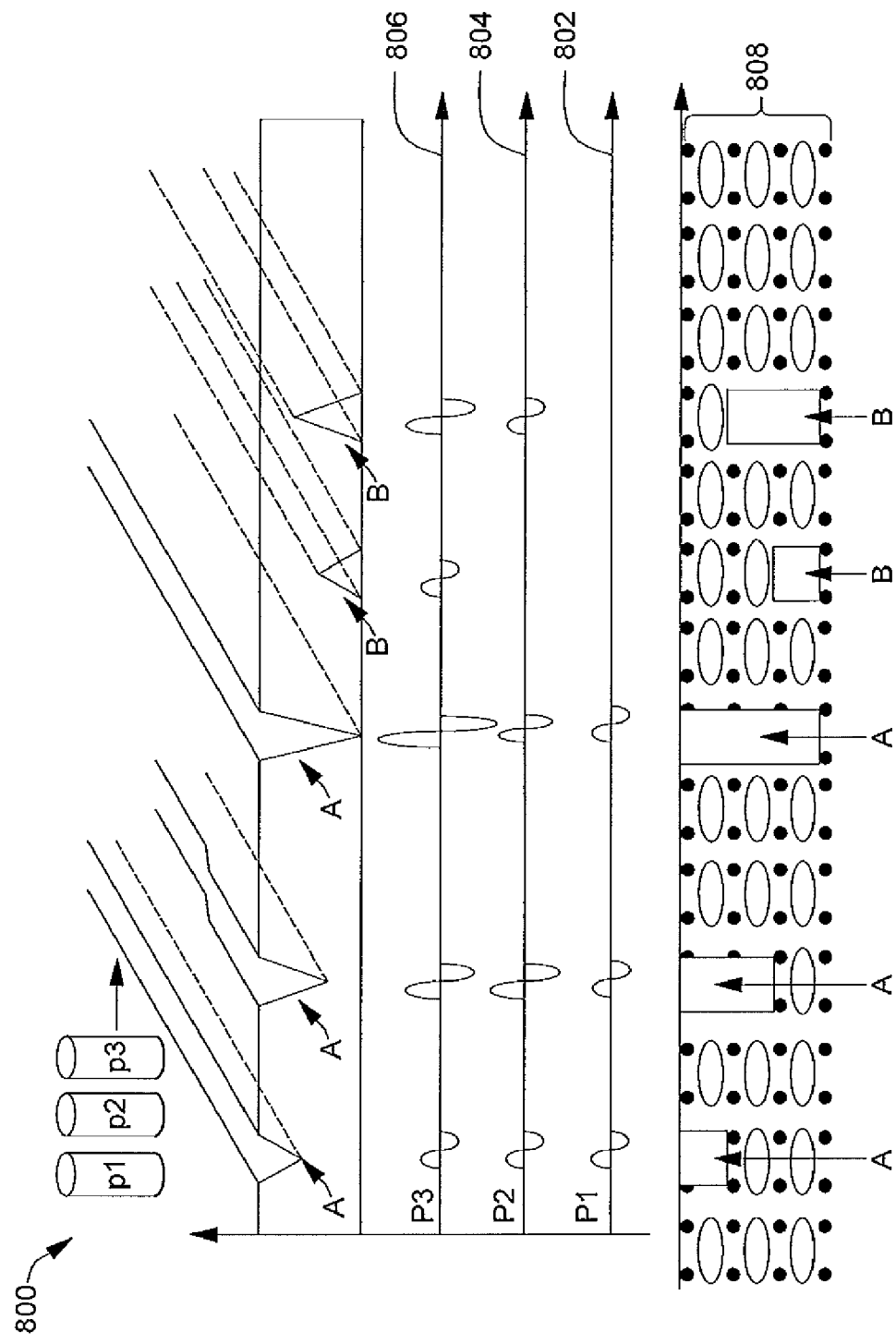
FIG. 8 is a graphical representation of an output of a sensor array according to an embodiment of the present invention, showing the output in response to various inconsistencies in a building material.

FIG. 8 illustrates a graphical representation 800 of a signal output 802, 804, 806 for an array of sensors p1, p2, p3, respectively. Each sensor p1, p2, p3 includes a plurality of sense windings and a drive winding. In certain embodiments, the sense windings are mounted and aligned for crack detection. Each of the sensors p1, p2, p3 is calibrated to have a different power level. The various power levels of the sensors p1, p2 ,p3 penetrate to different depths enabling the sensor array to detect cracks at different depths, thereby providing a two dimensional view into the road under test. A processor is used to analyze a data received by the sensor array to determine top-down cracks (represented in FIG. 8 with "A") or bottom-up cracks (represented in FIG. 8 with "B"). As a non-limiting example, multiple sensors can be placed along a line perpendicular to a transport vehicle's movement providing the third dimension. Alternately a single sensor with multiple sense windings, a single power drive winding, and a variable power control can provide the same information.

Figure 9:
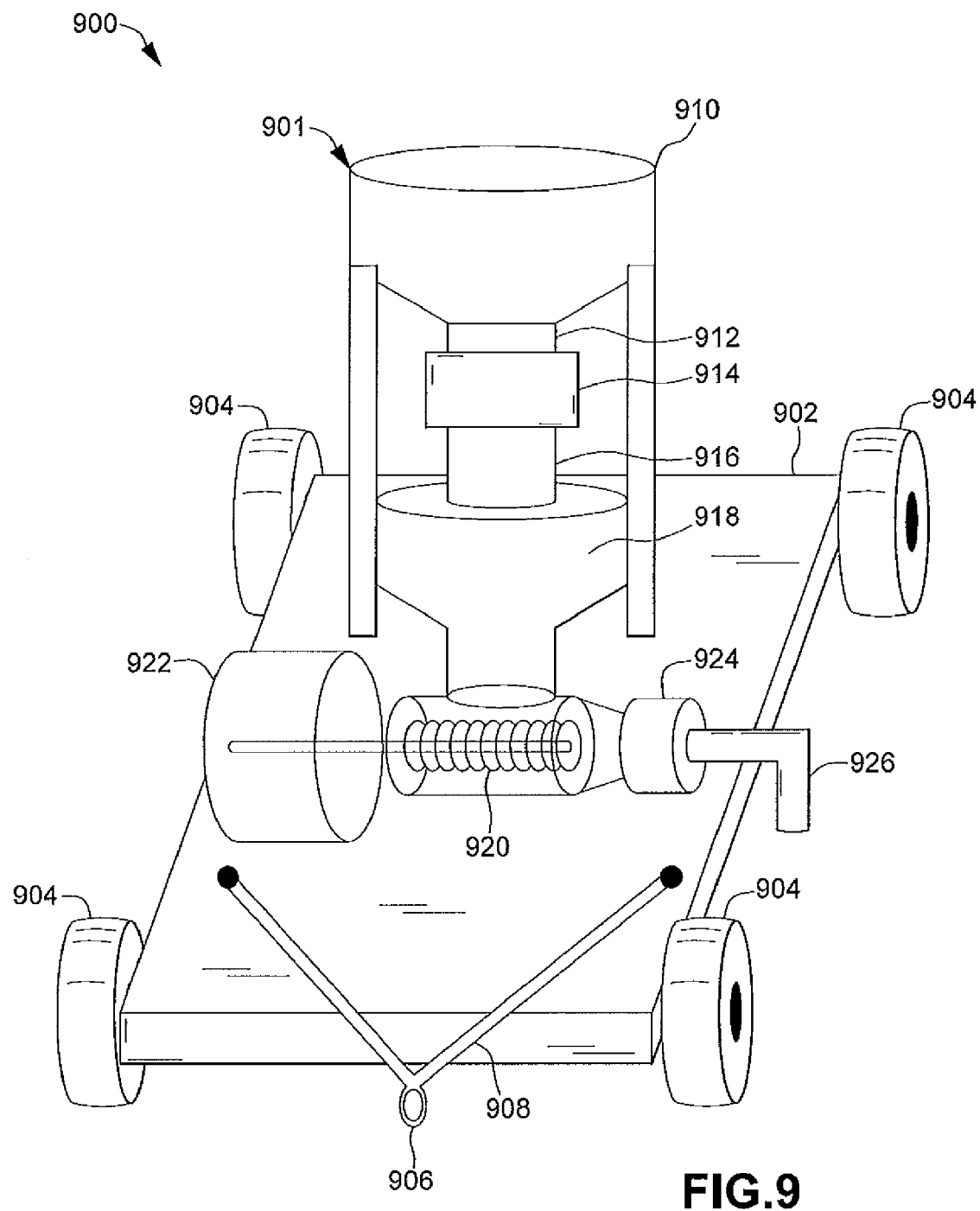
FIG. 9 is a schematic diagram of a portable testing apparatus for monitoring a building material according to an embodiment of the present invention.

FIG. 9 illustrates a portable magnetic flux tagging "drum" or "batch" mix tester, referred to as a portable batch tester 900. As a non-limiting example, the batch tester 900 may be used to test the quality of asphalt manufactured by a batch/drum mixer at a manufacturing plant. However, other building materials at any location may be tested.

The portable batch tester 900 includes a testing apparatus 901 disposed on a main body 902. In one embodiment, the main body 902 is coupled to a plurality of ground engaging wheels 904. A hitch device 906 is coupled to the main body 902 by a mounting bracket 908. However, it is understood that the portable batch tester 900 may be mounted on a trailer or built on a pick-up truck.

In the embodiment shown, the testing apparatus 901 includes a first hopper 910, a valve 912, a first batch sensor 914, a flow conduit 916, a second hopper 918, a heated feed screw 920, a motor 922 to drive the feed screw 920, a second batch sensor 924, and a dispensing conduit 926.

In use, the final mixture 147 is dispensed into the first hopper 910. In one embodiment, the flow conduit 916 is directed into a transport vehicle. As the final mixture 147 moves through the flow conduit 916 and into the transport vehicle, a shape of the flow conduit 916 minimizes a flow rate of the final mixture 147 to enable the first batch sensor 914 to monitor a mix ratio of the final mixture 147 before it is transported to the end-user. It is understood that the shape of the flow conduit 916 may have a varying diameter to control a flow rate of the final mixture 147. However, any shape may be used. It is further understood that the average value is related to the mix ratio while the standard deviation is related to how well it is mixed.

In the embodiment shown, the attached feed screw 920 enables the final mixture 147 to flow through the second batch sensor 924 before being dispensed onto a surface for road construction. It is understood that the feed screw 920 may guide the final mixture 147 to a transport vehicle after scanning or return he final mixture 147 to at least one of the hoppers 910, 918 and a batch mixer. Again, a variable diameter of the dispensing conduit 926 provides a constant back pressure which enables the second batch sensor 924 to accurately monitor a mix ratio and standard deviation. Alternately a plurality of sensors can be mounted on the transport vehicle during loading. It is understood that a plurality of sensor may also be mounted on a wall of the hoppers 910, 918 to monitor the final mixture 147 in real time, thereby notifying an operator if the final mixture 147 is optimally mixed.

In certain embodiments, a weight sensor may be used to perform a comparative test on a sample of the final mixture 147. Specifically, the sample is loaded into a mold until a pre-determined weight is attained. After loading, a force is applied to the sample through a piston-type compactor. The sample is compacted to a known force level and compared to a test performance in a laboratory setting. Each of the sensor devices used in the laboratory setting interfaces with a processor to display various graphs and data to aid the in laboratory test. For example, a sensor may be designed to measure the size of stones in a sample and thereby determine if the stones are properly mixed. Additionally, laboratory equipment enables real time monitoring of mix ratio, segregation, compaction, shear strength, and stone size, as well as crack detection and both horizontal and vertical scanning. In certain embodiments, it may be necessary to differentiate between testing masters after they are compacted with the laboratory compactor and using a portable-type lever-piston compactor which is able to apply less of a compaction as the laboratory equipped compactor. However, because of the ability to project densities over different compactions, the correct density may be determined at a given compaction. This can potentially be used at a construction site.

The present invention may be applied to all aspects of adding a tagged material for all construction and non-construction use of materials such as asphalt, cement, and various other products requiring mixing. Once a material is tagged, every manufacturing process is continuously monitored to ensure these processes remain within a desired specification.

The present invention enables finished products such as roads to be examined for changes. For example, if segregation occurs or a crack is caused by the volume of traffic examining the road from above the surface will clearly show a change in the asphalt which will inform the road engineer of potential failures or encourage preventive maintenance.

The present invention also provides the following benefits: quality checks after each manufacturing process will greatly reduce mixing, segregation and consistency errors; all tagged roads will be traceable to an easily reproducible master; specimens will be scanned for correct mix ratio and can be examined in real time as simulated vehicle loads are applied; the polymers, binder, stones, sand aggregate etc. are monitored to be accurately mixed within quality control limits; segregation will be continuously monitored, thereby minimizing any guess work on mixture quality and composition; sensors are not sensitive or affected by water or humidity which are common during road installation; below freezing temperature will not restrict the usage of the sensors enabling collection of data during the non-construction season, attaching a sensor to a moving vehicle will enable scanning the finished roads profile for segregation, compaction problems and cracks efficiently; sensors can be mounted permanently on a road surface to study changes in road conditions from usage; below surface sensors can provide real time loading response; collected data may be used for historical baseline and to provide feedback on the road's infrastructure; historical collection of mix ratio profiles may be used for evaluating changes in road conditions over time to assist in future preventative maintenance, planning and budget forecasting.

The present invention provides a comprehensive inspection of real time testing of the manufactured road, which ensures quality roads will last their theoretical lives without premature failures. This results in reduction of potholes, budgetary cost savings, less vehicle damage and various other benefits for taxpayers, communities, and businesses.

From the foregoing description, one ordinarily skilled in the art can easily ascertain the essential characteristics of this invention and, without departing from the spirit and scope thereof, make various changes and modifications to the invention to adapt it to various usages and conditions.

What is claimed is:

1. A method for monitoring a building material, the method comprising the steps of:
   a. mixing a predetermined amount of taggant particles with a predetermined first volume of a first component of a building material to prepare a first mixture in a first mixing device;
   b. providing a first sensor for generating a first sense signal representing an amount of taggant particles per unit volume of the first mixture flowing into a second mixing device;
   c. mixing a predetermined second volume of a second component of the building material with the first mixture to prepare a second mixture in the second mixing device;
   d. providing a second sensor generating a second sense signal representing an amount of taggant particles per unit volume of the second mixture flowing from the second mixing device;
   e. providing a processor for calculating a ratio of the volumes of the first and second components in the second mixture in response to the first and second sense signals;
   f. dispensing the second mixture onto a surface; and
   g. scanning the second mixture disposed on the surface.

2. The method according to claim 1, wherein at least one of the first mixing device and the second mixing device includes a feed screw.

3. The method according to claim 1, wherein at least one of the first mixing device and the second mixing device includes a feedback mix sensor.

4. The method according to claim 1, wherein at least one of the first sensor and the second sensor is an encircling sensor to receive a volume of a mixture therethrough.

5. The method according to claim 1, wherein the amount of taggant particles per unit volume is modeled by an equation.

6. The method according to claim 1, wherein the step of scanning the second mixture is executed by a winding sensor having a drive winding to generate a magnetic field.

7. The method according to claim 6, wherein the winding sensor includes at least one of a hall effect sensor and a sense winding for detecting at least one of a crack, a segregation, and a compaction density in the second mixture.

8. The method according to claim 6, wherein winding sensor include a first sense winding differentially wound with respect to a second sense winding.

9. The method according to claim 6, wherein the winding sensor includes a variable power control for adjusting a sensing depth thereof.

10. A method of monitoring a building material, the method comprising the steps of:
    a. mixing a predetermined amount of taggant particles with a predetermined first volume of a first component of a building material to prepare a first mixture in a first mixing device;
    b. providing a first sensor for generating a first sense signal representing an amount of taggant particles per unit volume of the first mixture;
    c. transporting the first mixture to a second mixing device;
    d. mixing a predetermined second volume of a second component of the building material with the first mixture to prepare a second mixture in the second mixing device;
    e. providing a second sensor generating a second sense signal representing an amount of taggant particles per unit volume of the second mixture flowing from the second mixing device;
    f. providing a processor for calculating a ratio of the volumes of the first and second components in the second mixture in response to the first and second sense signals;
    g. transporting the second mixture to a dispensing site;
    h. dispensing the second mixture onto a surface located at the dispensing site;
    i. compacting the second mixture on the surface to form a finished road; and
    j. scanning the finished road.

11. The method according to claim 10, wherein a means for transporting the first mixture and the second mixture includes a sensor for monitoring at least one of a mix ratio and a segregation of the first and second mixtures.

12. The method according to claim 10, wherein at least one of the first mixing device and the second mixing device includes a feed screw.

13. The method according to claim 10, wherein at least one of the first sensor and the second sensor is an encircling sensor to receive a volume of a mixture therethrough.

14. The method according to claim 10, further comprising the step of monitoring the second mixture during a compaction thereof.

15. The method according to claim 10, wherein the step of scanning the second mixture is executed by a winding sensor having a drive winding to generate a magnetic field.

* * * * *